US00PP17036P3

(12) United States Plant Patent
Yates

(10) Patent No.: US PP17,036 P3
(45) Date of Patent: Aug. 22, 2006

(54) ***PHYGELIUS* PLANT NAMED 'YAPYEL'**

(50) Latin Name: *Phygelius aequalis×rectus*
Varietal Denomination: YAPYEL1

(76) Inventor: Frederic Charles Yates, A. T. Yates & Son The Poplars Nursery, Congleton, Cheshire (GB), CW12 4SP ( * ) Notice: Subject to any disclaimer, the term of this patent is extended or adjusted under 35 U.S.C. 154(b) by 0 days.

(21) Appl. No.: 11/053,534

(22) Filed: Feb. 7, 2005

(65) Prior Publication Data

US 2005/0198720 P1 Sep. 8, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para

(57) ABSTRACT

A new cultivar of *Phygelius* named 'YAPYEL' that is characterized by a compact habit with strong basal branching, and yellow pendulous flowers. In combination these traits set 'YAPYEL' apart from all other existing varieties of *Phygelius* known to the inventor.

2 Drawing Sheets

Genus: *Phygelius.*
Species: *aequalis×rectus.*
Denomination: 'YAPYEL'.

BACKGROUND OF THE INVENTION

The present invention relates to a new and distinct cultivar of *Phygelius,* that is grown for its ornamental pendulous yellow flowers. The new cultivar is known botanically as *Phygelius aequalis×rectus* and will be referred to hereinafter by the cultivar name 'YAPYEL'.

The inventor has been interested for some fifteen years in the genus *Phygelius,* and has collected many named and unnamed plants of the three species of *Phygelius,* namely *Phygelius aequalis, Phygelius capensis,* and the inter-specific *Phygelius×rectus* (*P. aequalis×capensis*). The inventor has recognized that the genus would be more widely produced and sold commercially if its growth habit would be shorter and more sturdy with natural self-branching. The species of *Phygelius* and most of the available cultivars, exhibit a vigorous upright growth, such that, although the flowers are much admired, the habit of the plant itself is unappealing to some gardeners. Although it is possible to induce branching and shorter internodes by the application of plant growth regulators during the production cycle, the effect of such applications wears off as the season proceeds and the plants fail to remain upright without staking or support from adjacent plants.

'YAPYEL' was bred by the inventor in a cultivated area of Cheshire, England. 'YAPYEL' is one of three varieties selected for release from the same breeding program. The companion varieties 'YAPCOR' (U.S. Plant patent application Ser. No. 11/053,252) and 'YAPOR' (U.S. Plant patent application Ser. No. 11/053,242) are the subject of contemporaneous applications. The plant habits of 'YAPYEL', 'YAPCOR' and 'YAPOR' are similarly compact, and their flower colors are respectively yellow, dark coral pink, and salmon-orange. 'YAPYEL' arose as follows:

In 1990, the inventor purchased a single plant of *Phygelius* labeled simply as *Phygelius aequalis,* that is, without a cultivar designation. This plant carried the characteristic pale yellow flowers of the species *Phygelius aequalis* but the inventor was attracted by its uncharacteristic compact habit. The inventor allowed the plant to run to seed, then harvested a quantity of seed which was sown and grown out as a seedling population. The inventor selected a single plant from this population and named it "Compact Primrose". Compact Primrose was retained by the inventor as a useful parent for a future breeding program aimed at producing a series of complementary flower colors on plants with natural compactness and good branching. Compact Primrose grows to a height of 40 cm in the season whereas plants of the genus typically achieve heights of or exceeding 70 cm in one growing season. Compact Primrose, which has never been made available to the public, has been maintained and renewed by vegetative propagation at the inventor's nursery in Somerford, Cheshire, England.

In 1998, the inventor commenced his program to derive a series of compact cultivars of *Phygelius.* The inventor selected a single plant of *Phygelius×rectus* 'Moonraker' (unpatented) for hand cross-pollination with Compact Primrose. The inventor used flowers from both plants as both pollen donors and pollen receptors and seed was collected from both plants for sowing and seedling grow-out in 1999. From plants selected in 1999 and vegetatively propagated and grown to flowering in 2000, the inventor selected 'YAPYEL' as presenting the best combination of improved plant habit and distinct and clear flower color and overall compatibility with the contemporaneously selected varieties 'YAPCOR' and 'YAPOR' whose breeding had followed the same procedure, namely the use of a promising parent as alternate parent with Compact Primrose as described in the relative applications 'YAPCOR' and 'YAPOR').

Although 'YAPYEL' is similar in flower color to the inventor's unreleased parent named "Compact Primrose", 'YAPYEL' is slightly taller and is more closely compatible in overall shape of plant and density of inflorescence with its intended series companions, 'YAPCOR' and 'YAPOR'. The alternate parent, *Phygelius×rectus* 'Moonraker' is approximately 70 cm in overall height with sparse basal branching and yellow flowers, whereas 'YAPYEL' is approximately 45 cm in height, exhibits multiple branching and similar yellow flowers. The closest varieties in overall habit known to the inventor are the inventor's varieties 'YAPCOR' and 'YAPOR' which differ in flower coloration.

'YAPYEL' was first asexually propagated by the inventor in Cheshire, England in 1999 using softwood cuttings. Since that time, under careful observation, the distinguishing characteristics have been determined stable and uniform in successive generations.

SUMMARY OF THE INVENTION

The following represent the distinguishing characteristics of the new *Phygelius* cultivar 'YAPYEL'. In combination these traits set 'YAPYEL' apart from all other existing varieties of *Phygelius* known to the inventor. 'YAPYEL' has not been tested under all possible conditions and phenotypic differences may be observed with variations in environmental, climatic, and cultural conditions, however, without any variance in genotype.

1. *Phygelius* 'YAPYEL' is 45 cm in height and approximately as wide.
2. *Phygelius* 'YAPYEL' branches naturally from the base when grown in a container.
3. *Phygelius* 'YAPYEL' may spread by underground stolons when planted in the ground in conditions where it remains perennial.
4. *Phygelius* 'YAPYEL' exhibits pendulous clusters of yellow flowers in summer and fall.
5. *Phygelius* 'YAPYEL' tolerates temperatures of minus 50 Celsius to minus 8° Celsius.

BRIEF DESCRIPTION OF THE DRAWINGS

The accompanying color photographs illustrate the distinguishing traits of the new *Phygelius* cultivar 'YAPYEL'. The plant photographed was in its first season of growth at the inventor's nursery in Cheshire, England. The plant was started as a cutting in early spring and potted into a 1 liter pot in a cool greenhouse (temperature maintained at or above 10 degrees Celsius) prior to being stood outside after the risk of frost.

The drawing labeled as FIG. 1 illustrates a plant of 'YAPYEL' at the time of removal from the greenhouse, around May.

The drawing labeled as

Figure 1:
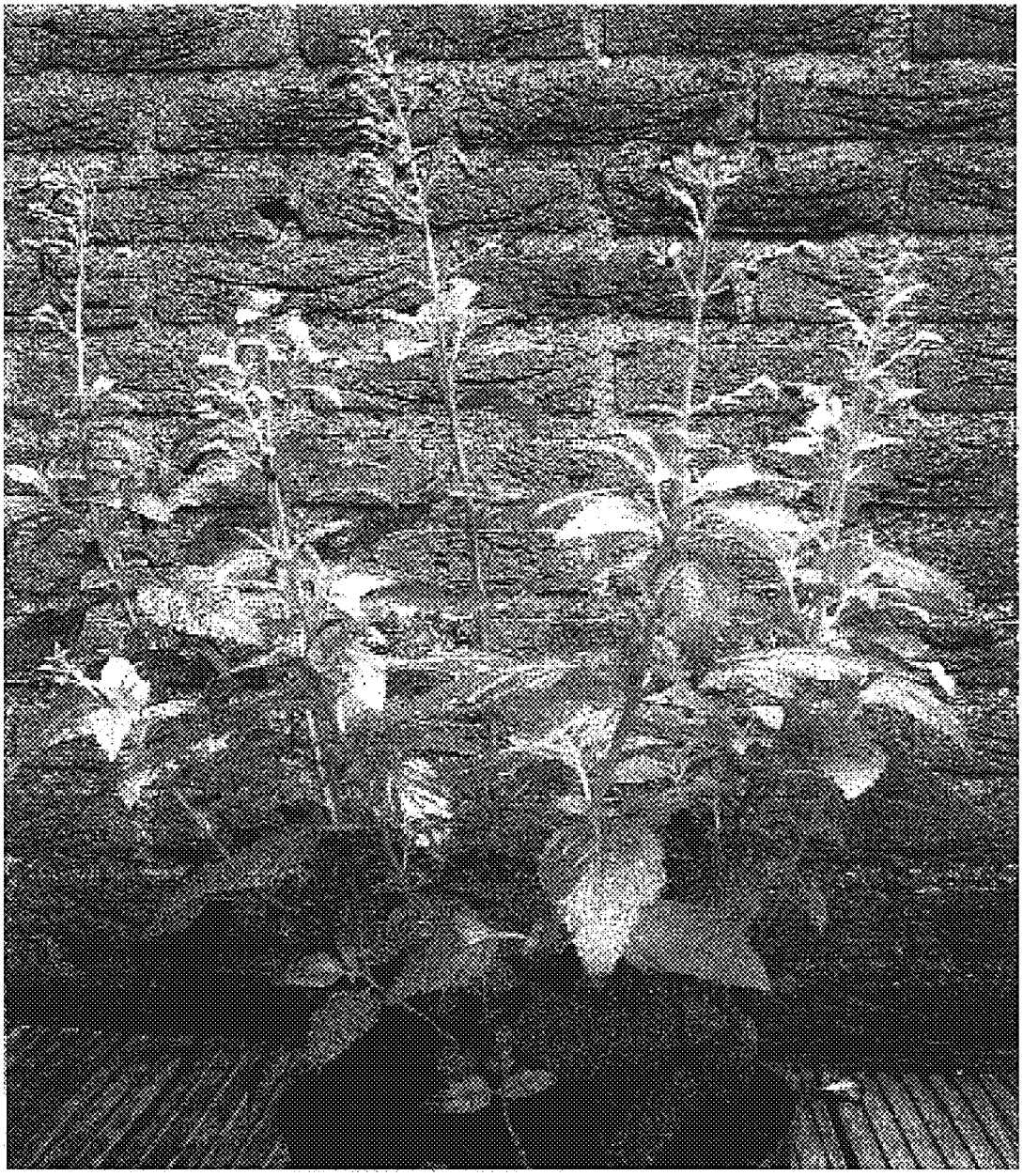
FIG. 1 depicts the strong basal branching habit of 'YAPYEL' and flower stems with flowers still in tight bud.
Figure 2:
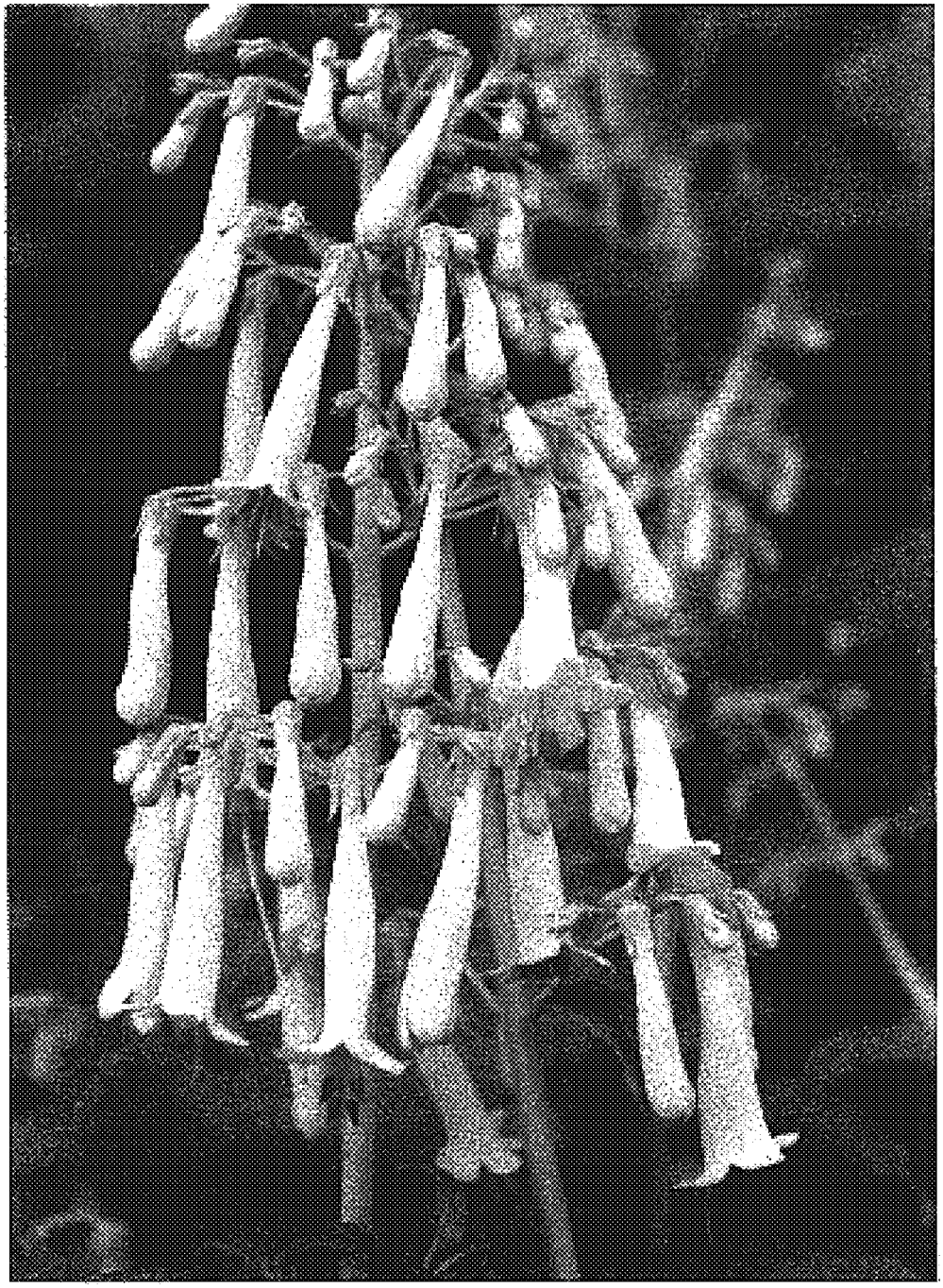

FIG. 2 illustrates a close-up view of an inflorescence of 'YAPYEL'. FIG. 2 depicts the yellow corolla tubes and the exserted stamens.

All photographs were taken using conventional techniques and are considered reasonably representative of the foliage and flower colors of 'YAPYEL'.

BOTANICAL DESCRIPTION OF THE PLANT

The following is a detailed description of the *Phygelius* cultivar named 'YAPYEL'. Data was collected from a plant which was started as a cutting in early spring and potted into a 1 liter pot in a cool greenhouse (temperature maintained at or above 10 degrees Celsius) prior to being stood outside. Color determinations are in accordance with the 2001 Edition of The Royal Horticultural Society Colour Chart except where general color terms of ordinary dictionary significance are used.

Botanical classification:
- *Genus.*—*Phygelius.*
- *Species.*—*aequalis*×*rectus.*
- *Denomination.*—'YAPYEL'.

Common name: Cape Fuchsia.

Uses: Herbaceous perennial in temperate or Mediterranean climates; container annual or component in mixed annual containers in all climates.

Parentage: 'YAPYEL' resulted from the cross-pollination between an unreleased plant of *Phygelius aequalis* known to the inventor as 'Compact Primose', and *Phygelius*× *rectus* 'Moonraker'.

Type: Perennial.

Vigor: Moderate to vigorous: makes approximately 15 cm growth per month.

Habit: Upright.

Shape: Foliage makes broad inverted triangle.

Height: 45 cm.

Width: 40 cm.–45 cm.

Hardiness: USDA Zone 7B.

Propagation: Softwood cuttings.

Root system: Fibrous.

Soil: Plant in well-drained soils.

Sunlight: Plant in full sunlight.

Plant sexuality: Bisexual.

Time to initiate roots: 2 weeks are required for an initial cutting to produce roots.

Crop time: Approximately 25 weeks are required to produce a finished flowering plant from a rooted cutting.

Seasonal interest: Flowers in summer and fall.

Susceptibility or resistance to pests and diseases: None noted for the genus or for 'YAPYEL' in particular.

Stem:
- *Basal branching.*—Moderate: 5–8 stems typically grow from base. Strong apical dominance: slight lateral branching until inflorescence development.
- *Lateral branching* (*without pinching*).—Slight.
- *Basal stems length.*—25 cm–35 cm including inflorescence.
- *Basal stems diameter.*—Varies widely: between 3 mm–6 mm at the base to between 2 mm–4 mm below inflorescence.
- *Lateral branch length.*—5 cm–10 cm at stage of fully budded inflorescence on basal stems.
- *Lateral branch diameter.*—3 mm.
- *Internode length.*—4 cm. between nodes.
- *Shape.*—Quadrangular; older stems almost rounded.
- *Surface.*—Glabrous, slightly glossy.
- *Pubescence.*—None.
- *Texture.*—Young stems covered with lanceolate lenticels; length 0.5 mm, width 0.2 mm, coloration 145C.
- *Stem color.*—144B; older stems 152D.

Foliage:
- *Type.*—Evergreen.
- *Leaf arrangement.*—Opposite.
- *Leaves per lateral branch.*—Averages 14 (7 pairs).
- *Leaf division.*—Simple.
- *Leaf shape.*—Ovate.
- *Leaf margin.*—Serrate, averages 3.5 teeth per cm.
- *Leaf base.*—Short attenuate.
- *Leaf apex.*—Acute.
- *Leaf venation.*—Pinnate.
- *Vein color* (*adaxial surfaces*).—144A.
- *Vein color* (*abaxial surface*).—144B.

*Leaf attachment.*—Petiolate.
*Petiole dimensions.*—1.8 cm. in length and 2 mm. in diameter.
*Petiole color.*—144A.
*Petiole bracts.*—2 present on each petiole; Shape: narrow ovate; Apex: acute; Base: cuneate; Margins: entire; Color: between N186C and 200A.
*Stipules.*—Absent.
*Leaf length.*—7 cm. in length.
*Leaf width.*—4 cm. in width.
*Leaf color* (*young leaves, adaxial surface*).—Between 141B and 143A.
*Leaf color* (*young leaves, abaxial surface*).—144A.
*Leaf color* (*mature leaves, adaxial surface*).—137A.
*Leaf color* (*mature leaves, abaxial surface*).—147B.
*Leaf surfaces* (*adaxial and abaxial*).—Smooth, glabrous. Pubescence absent.
*Foliar fragrance.*—Absent.

Flower:
*Natural flowering season.*—Summer into fall (late June to late October).
*Inflorescence.*—Compound terminal cyme.
*Inflorescence height.*—15 cm–17 cm.
*Inflorescence width.*—13 cm–15 cm.
*Quantity of flowers per inflorescence.*—Approximately 70.
*Quantity of flowers and buds per plant.*—Approximately 550 at peak flowering.
*Form.*—Solitary.
*Flower shape.*—Tubular with five lobes.
*Persistent or self-cleaning.*—Self-cleaning.
*Aspect.*—Pendulous.
*Peduncle strength.*—Strong: flowers do not detach in wind.
*Angle of peduncle to stem.*—55° from the vertical.
*Peduncle length.*—18.7 cm.
*Peduncle diameter.*—2.5 mm.
*Surface of peduncle.*—Glabrous.
*Color of peduncle.*—Varies between 144A and 144B.
*Pedicels.*—Present.
*Pedicel dimensions.*—1.7 cm in length, 1 mm in diameter.
*Pedicel color.*—Varies between 144A and 144B.
*Bud.*—Tubular and nutant.
*Bud length.*—2.7 cm.
*Bud diameter.*—5 mm.
*Bud shape.*—Narrow oblong-obovate, curved.
*Bud color.*—Between 5C and 5D, tip slightly darker, 5C.
*Bud rate of opening.*—Approximately 5 days from tight bud to fully open and extended flower.
*Diameter of flower* (*at base*).—6 mm.
*Diameter of flower* (*apex*).—1.6 cm including lobes.
*Depth of flower* (*corolla tube*).—5.1 cm. in depth.
*Length of flower* (*tube and lobes*).—4 cm. in length.
*Shape.*—Tubular with five lobes.
*Fragrance.*—None.
*Lastingness of single flower.*—1 week.
*Petals.*—Five in number.
*Fused or unfused.*—Petals are fused, except upper 15% of petals are free.
*Petal shape.*—Upper (free) part of petal is broad ovate.
*Petal margin.*—Entire, revolute.
*Petal apex.*—Broad acute.
*Petal length.*—4 cm.
*Petal width* (*unfused part*).—5 mm.
*Petal* (*corolla tube*) *color, outer surface.*—Varies between 5C and 5D throughout, including lobes.
*Petal* (*corolla tube*) *color, inside surface.*—5D.
*Calyx shape.*—Campanulate.
*Calyx length.*—6 mm.
*Calyx diameter.*—1.1 mm.
*Calyx surface.*—Glabrous.
*Sepals.*—Four in number.
*Fused or unfused.*—Sepals are basally fused.
*Sepal appearance.*—Smooth, dull.
*Sepal arrangement.*—Campanulate.
*Sepal length.*—7 mm.
*Sepal width.*—3 mm.
*Sepal margin.*—Entire.
*Sepal apex.*—Acute.
*Sepal base.*—Fused, lower 20%.
*Sepal color, immature, adaxial surface.*—N199A.
*Sepal color, immature, abaxial surface.*—200B.
*Sepal color, mature, adaxial surface.*—191C and 191D.
*Sepal color, mature, abaxial surface.*—191B.

Reproductive organs:
*Stamens.*—Four, exserted by approximately 5 mm–8 mm.
*Stamen dimensions.*—1 cm. in length and 2 mm in diameter.
*Stamen color.*—61A.
*Filament.*—Implanted in tube, length 15 mm.
*Anther attachment.*—Basifixed.
*Anther shape.*—Oval.
*Anther dimensions.*—Length and width between 2.5 mm and 3 mm.
*Anther color.*—160D.
*Pollen amount.*—Moderate.
*Pollen color.*—Varies between 165C and 165D.
*Pistil.*—One.
*Dimensions of pistil.*—5 cm. in length and less than 1 mm. in diameter.
*Stigma shape.*—Club-shaped.
*Stigma color.*—189A.
*Style length.*—5 cm.
*Style color.*—Varies between 154C and 154D, tip slightly darker.
*Ovary position.*—Superior.
*Ovary color.*—146C.

Capsule and seed:
*Capsule.*—Color as for stem, shape oval, pointed, opens like a beak. Dimensions: approximately 1 cm in length and 5 mm in width. Texture: Rough with lateral ribs.
*Small.*—Approximately 200–500 per capsule. Spherical, less than 0.5 mm diameter, dark brown, gritty texture.

It is claimed:

1. A new and distinct variety of *Phygelius* plant named 'YAPYEL' as described and illustrated.

* * * * *